(12) United States Patent
Ikeda et al.

(10) Patent No.: US 7,196,193 B2
(45) Date of Patent: Mar. 27, 2007

(54) METHOD FOR PREPARING 6-AMINOMETHYL-6, 11-DIHYDRO-5H-DIBENZ[B,E]AZEPINE

(75) Inventors: Shin Ikeda, Haramachi (JP); Yasuhiro Takahashi, Haramachi (JP)

(73) Assignee: Konica Minolta Chemical Co., Ltd., Tokyo (JP)

( * ) Notice: Subject to any disclaimer, the term of this patent is extended or adjusted under 35 U.S.C. 154(b) by 391 days.

(21) Appl. No.: 10/510,008

(22) PCT Filed: Apr. 11, 2002

(86) PCT No.: PCT/JP02/03602

§ 371 (c)(1),
(2), (4) Date: Sep. 30, 2004

(87) PCT Pub. No.: WO03/084932

PCT Pub. Date: Oct. 16, 2003

(65) Prior Publication Data

US 2005/0209215 A1   Sep. 22, 2005

(51) Int. Cl.
*C07D 223/20* (2006.01)
*C07D 403/06* (2006.01)

(52) U.S. Cl. .................................... 540/587
(58) Field of Classification Search ................. 540/587
See application file for complete search history.

(56) References Cited

U.S. PATENT DOCUMENTS 5,312,916 A * 5/1994 Schneider .................. 540/579

FOREIGN PATENT DOCUMENTS

| JP | 2001-131177 | * | 5/2001 |
| JP | 2002-193939 | * | 7/2002 |
| JP | 2002-193940 | * | 7/2002 |

* cited by examiner

*Primary Examiner*—Brenda Coleman
(74) *Attorney, Agent, or Firm*—Lucas & Mercanti, LLP

(57) ABSTRACT

A production method of 6-aminomethyl-6,11-dihydro-5H-dibenz[b,e]azepin characterized in that said compound is produced via N-[(6,11-dihydro-5H-dibenz[b,e]azepin-6-yl)methyl]-o-hydroxymethylbenzamide which is prepared by reducing 2-(11H-dibenz[b,e]azepin-6-ylmethyl)-1H-isoindole-1,3(2H)-dione employing a metal hydride or a metal hydride complex in a water based alcohol, and N-[(6,11-dihydro-5H-dibenz[b,e]azepin-6-yl)methyl]-o-hydroxymethylbenzamide which is useful for the aforesaid production method.

5 Claims, 1 Drawing Sheet

METHOD FOR PREPARING 6-AMINOMETHYL-6, 11-DIHYDRO-5H-DIBENZ[B,E]AZEPINE

This application is a 371 National Phase entry of PCT/JP02/03602 filed Apr. 11, 2002.

TECHNICAL FIELD

The present invention relates to a novel production method of 6-aminomethyl-6,11-dihydro-5H-dibenz[b,e]azepin which is markedly important as an intermediate to produce 3-amino-9,13b-dihydro-1H-dibenz[c,f]imidazo[1,5a]azepin hydrochloric acid salt which is therapeutically useful while characterized by antiallergic and antihistaminic actions.

BACKGROUND

6-Aminomethyl-6,11-dihydro-5H-dibenz[b,e]azepin is an important compound as a raw material of medicines. Known as production methods of the aforesaid compound is a method in which 6-cyano-11H-dibenzo[b,e]azepin is allowed to react, in THF, with lithium aluminum hydride and aluminum hydride prepared employing 100 percent sulfuric acid (Arzneim.-Forsch., 40, 4, 440, (1990) and Japanese Patent Publication No. 3-66311.

However, the aforesaid synthesis method necessitates an anhydrous THF solvent which results in heavy load in terms of cost and includes time consuming operations such as filtration of an excessive amount of inorganic substances deposited after the reaction.

Further, known is a method in which 6-phthalimidomethyl-6,11-dihydro-5H-dibenz[b,e]azepin is isolated, which is formed by hydrogenating 2-(1H-dibenz[b,e]azepin-6-yl-methyl-1H-isoindole-1,3(2H)-dione employing formic acid as well as palladium carbon, and subsequently is subjected to hydrazine decomposition. (Japanese Patent Publication Open to Public Inspection No. 4-346988).

However, since this method uses hydrazine, which is a carcinogenic substance, in the industrial production, operators' safety becomes a problem. Further, isolation is required between the hydrogenation and the hydrazine decomposition. During industrial scale production, it is well known that a decrease in isolation is desirable.

SUMMARY OF THE INVENTION

An object of the present invention is to provide a production method which enables to avoid the use of hazardous substances as well as to shorten the process in the synthesis of 6-aminomethyl-6,11-dihydro-5H-dibenz[b,e]azepin from 2-(11H-dibenz[b,e]azepin-6-ylmethyl)-1H-isoindole-1,3(2H)-dione.

The inventors of the present invention conducted diligent investigations to overcome the aforesaid problems. As a result, it was discovered that 2-(11H-dibenz[b,e]azepin-6-ylmethyl)-1H-isoindole-1,3(2H)-dione was allowed to react with a metal hydride or a metal hydride complex, whereby it was possible to reduce the imine portion as well the phthalimide portion in one vessel. It is known in prior art (Tetrahedron Letters, 25, 20, 2093, (1984)) that phthalimide is subjected to deprotection (or cleavage) employing metal hydrides. However, it was surprising that it was possible to simultaneously reduce not only the phthalimide portion but also the imine portion in the same molecule, and even when a water based solvent was employed, the imine portion was reduced to amine resulting in almost no hydrolysis. Further, it was discovered that formed N-[(6,11-dihydro-5-Hdibenz[b,e]azepin-6-yl)methyl]-o-hydroxymethylbenzamide was readily decomposable without an isolation process, and 6-aminomethyl-6,11-dihydro-5H-dibenz[b,e]azepin could be prepared in one vessel. Thus, the present invention was achieved.

Namely, the present invention include:

(1) a production method of 6-aminomethyl-6,11-dihydro-5H-dibenz[b,e]azepin via N-[(6,11-dihydro-5H-dibenz[b,e]azepin-6-yl)methyl]-o-hydroxymethylbenzamide which is prepared by allowing 2-(11H-dibenz[b,e]azepin-6-ylmethyl)-1H-isoindole-1,3(2H)-dione to react with a metal hydride or a metal hydride complex, (2) N-[(6,11-dihydro-5H-dibenz[b,e]azepin-6-yl)methyl]-o-hydroxymethylbenzamide, (3) a production method of 6-aminomethyl-6,11-dihydro-5H-dibenz[b,e]azepin, described in (1) in which the metal hydrides or the metal hydride complex is boron hydrides, (4) a production method of 6-aminomethyl-6,11-dihydro-5H-dibenz[b,e]azepin, described in (1), characterized in that an alcohol or a water based alcohol is employed as a solvent, and (5) a production method of 6-aminomethyl-6,11-dihydro-5H-dibenz[b,e]azepin, described in (1), characterized in that N-[(6,11-dihydro-5H-dibenz[b,e]azepin-6-yl)methyl]-o-hydroxymethylbenzamide is processed with a acid or a base.

DESCRIPTION OF THE PREFERRED EMBODIMENTS

Figure 1:
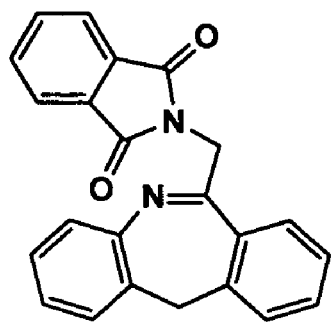
FIG. 1 shows 2-(11H-dibenz[b,e]azepin-6-ylmethyl)-1H-isoindole-1,3(2H)-dione.
Figure 2:
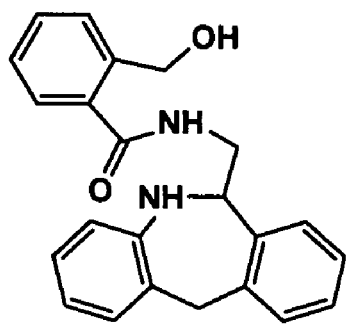
FIG. 2 shows N-[(6,11-dihydro-5H-dibenz[b,e]azepin-6-yl)methyl]-o-hydroxymethylbenzamide.
Figure 3:
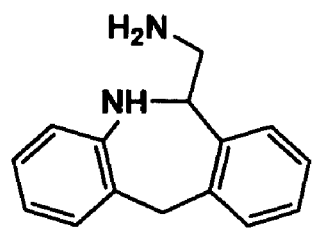
FIG. 3 shows 6-aminomethyl-6,11-dihydro-5H-dibenz[b,e]azepin.

In the present invention, the reaction is conducted by successively charging raw materials, a solvent, and a metal hydride or a metal hydride complex into a reaction vessel. Stirring is continued until completion of the reaction. Thereafter, an acid or a base is added, and the resulting mixture is heated while stirring to undergo decomposition. Subsequently, by employing a method such as extraction, 6-aminomethyl-6,11-dihydro-5H-dibenz[b,e]azepin is obtained in the form of a syrup. If desired, it is possible to obtain it in the form of crystals by forming a salt with a mineral acid or an organic acid. Further, after formation the salt, it is possible to purify the resulting crystals by extracting impurities employing an organic solvent.

The used amount of a metal hydride or a metal hydride complex is customarily 6–60 times with respect to the theoretical amount, is preferably 12–30 times, and is most preferably 12–20 times. When it is less than 6 times, unreactants tend to remain, while when it exceeds 60 times, such an added amount is not economically preferable. Addition may be carried out in the form of powder, or after dissolved in a solvent, the resulting solution may be added dropwise.

Examples of reaction solvents employed are alcohols as well as water base alcohols. Preferred alcohols include n-butanol, isobutanol, n-propanol, isopropanol, ethanol, and methanol, as well as solvent mixtures thereof. Of these, particularly preferred is isopropanol. The concentration of water in a water based alcohol is customarily 1–99 percent by weight, but is particularly preferably 18 percent by weight. The used amount of a solvent (including water) is customarily 1–50 times by volume with respect to the weight of 2-(11H-dibenz[b,e]azepin-6-ylmethyl)-1H-isoindole-1,3(2H)-dione, is preferably 2–20 times, and is most preferably 10–15 times.

If desired, in order to accelerate the reaction, added may be inorganic salts. Even though not particularly limited, preferable inorganic solts are zinc chloride, magnesium chloride, and cobalt chloride.

The reaction temperature is 0° C.—refluxing temperature, and is preferably 30–40° C. The reaction at a temperature of 0° C. or less is not economical due to excessively low production rate.

N-[6,11-dihydro-5H-dibenz[b,e]azepin-6-yl]methyl]-o-hydroxymethylbenzamide may undergo decomposition in the presence of either acids or bases. Examples of acids employed may be mineral acids as well as organic acids. Of these, preferred are hydrochloric acid, sulfuric acid, methanesulfonic acid, acetic acid, and formic acid, and hydrochloric acid as well as acetic acid is particularly preferred. Examples of bases employed may be inorganic bases as well as organic bases. Of these, preferred are salts or hydroxides of alkaline metals as well as alkylamines, and sodium hydroxide is particularly preferred.

EXAMPLES

The present invention will now be specifically described with reference to examples. However, the present invention is not limited to these.

A raw material, 2-(11H-dibenz[b,e]azepin-6-ylmethyl)-1H-isoindole-1,3(2H)-dione was synthesized based on the method described in J. Heterocycle. Chem., 17, 2, 341, (1980).

Example 1

Charged into a 100 ml flask fitted with a stirrer, a reflux cooler, and a thermometer were 3.0 g (8.5 millimoles) of 2-(11H-dibenz[b,e]azepin-6-ylmethyl-1H-isoindole-1,3 (2H)-dione, 45.0 ml of isopropanol, and 7.5 ml of water. Thereafter, while stirring at room temperature, 1.3 g (35.1 millimoles) of sodium borohydride was added over 30 minutes while maintaining a maximum temperature of 30° C. After addition, the resulting content, in the form of a white slurry, was stirred at room temperature for 24 hours. After decomposing the residual sodium borohydride by dripping 10.7 g of acetic acid into the resulting reaction composition at room temperature, the resulting mixture was stirred at 80° C. for 1.5 hours and was left standing until its interior temperature was allowed to equilibrate to room temperature. Subsequently, 24.0 ml of water as well as 24.0 ml of toluene was added and the resulting mixture was subjected to extraction by adjusting the pH to 11 by addition of a 25 percent NaOH solution. The resulting extract was concentrated under vacuum, whereby 3.1 g of a brown syrup was prepared. The resulting brown syrup was dissolved in 1.8 ml of methanol, followed by dripping of 0.89 g of fumaric acid dissolved in 18 ml of methanol. After confirming the deposition of crystals at room temperature, stirring was carried out at 0° C. for 3 hours and filtration under vacuum was carried out. The resulting cake was washed with 1.0 ml of cooled methanol and subsequently dried.

Yield: 2.0 g of 6-aminomethyl-6,11-dihydro-5H-dibenz[b,e]azepin-fumaric acid salt (69.0 percent of the theoretical amount)

Example 2

Charged into a 300 ml flask fitted with a stirrer, a reflux cooler, and a thermometer were 3.0 g (8.5 millimoles) of 2-(11H-dibenz[b,e]azepin-6-ylmethyl-1H-isoindole-1,3 (2H)-dione, 45.0 ml of isopropanol, and 7.5 ml of water. Thereafter, while stirring at room temperature, 1.3 g (35.1 millimoles) of sodium borohydride was added over 30 minutes while maintaining a maximum temperature of 30° C. After addition, the resulting content in the form of a white slurry was stirred at room temperature for 24 hours. After decomposing the residual sodium borohydride by adding 140 ml of 1 N hydrochloric acid into the resulting reaction composition, the resulting mixture was stirred at 80° C. for 1.5 hours and was left standing until its interior temperature was allowed to equilibrate to room temperature. Subsequently, 24.0 ml of toluene was added. After separation, extraction was carried out employing 24.0 ml of toluene by adjusting the pH of the water layer to 11 by addition of a 25 percent NaOH solution. The resulting extract was concentrated under vacuum, whereby 3.0 g of a brown syrup was prepared. The resulting brown syrup was dissolved in 1.8 ml of methanol, followed by dripping of 0.89 g of fumaric acid dissolved in 18 ml of methanol. After confirming the deposition of crystals at room temperature, stirring was carried out at 0° C. for 3 hours and filtration under vacuum was carried out. The resulting cake was washed with 1.0 ml of cooled methanol and subsequently dried.

Yield: 2.2 g of 6-aminomethyl-6,11-dihydro-5H-dibenz[b,e]azepin-fumaric acid salt (76.1 percent of the theoretical amount)

Example 3

Charged into a 300 ml flask fitted with a stirrer, a reflux cooler, and a thermometer were 3.0 g (8.5 millimoles) of 2-(11H-dibenz[b,e]azepin-6-ylmethyl-1H-isoindole-1,3 (2H)-dione, 0.45.0 ml of isopropanol, and 7.5 ml of water. Thereafter, while stirring at room temperature, 1.3 g (35.1 millimoles) of sodium borohydride was added over 30 minutes while maintaining a maximum temperature of 30° C. After addition, the resulting content in the form of a white slurry was stirred at room temperature for 24 hours. After decomposing the residual sodium borohydride by dripping 5.0 ml of MeOH into the resulting reaction composition, 3.0 ml of a 25 percent NaOH solution was added, the resulting mixture was stirred at 80° C. for 1.5 hours and was left standing until its interior temperature was allowed to equilibrate to room temperature. Subsequently, 24.0 ml of toluene was added. After separation, the resulting extract was concentrated under vacuum, whereby 3.0 g of a brown syrup was prepared. The resulting brown syrup was dissolved in 1.8 ml of methanol, followed by dripping of 0.89 g of fumaric acid dissolved in 18 ml of methanol. After confirming the deposition of crystals at room temperature, stirring was carried out at 0° C. for 3 hours and filtration under vacuum was carried out. The resulting cake was washed with 1.0 ml of cooled methanol and subsequently dried.

Yield: 2.1 g of 6-aminomethyl-6,11-dihydro-5H-dibenz[b,e]azepin-fumaric acid salt (72.4 percent of the theoretical amount)

Example 4

Charged into a 100 ml flask fitted with a stirrer, a reflux cooler, and a thermometer were 3.0 g (8.5 millimoles) of 2-(11H-dibenz[b,e]azepin-6-ylmethyl-1H-isoindole-1,3 (2H)-dione, 45.0 ml of isopropanol, and 7.5 ml of water. Thereafter, while stirring at room temperature, 1.3 g (35.1 millimoles) of sodium borohydride was added over 30 minutes while maintaining a maximum temperature of 30° C. After addition, the resulting content in the form of a white slurry was stirred at room temperature for 24 hours. The residual sodium borohydride was decomposed by dripping 5.0 ml of MeOH to the resulting liquid reaction composition at room temperature. Crystals deposited by dripping 40 ml of water were colleted by filtration and dried whereby N-[(6,11-dihydro-5H-dibenz[b,e]azepin-6-yl)methyl]-o-hydroxymethylbenzamide was isolated.

1H-NMR (DMSO) δ3.7–3.8 (m, 1H), 3.9–4.1 (m, 2H), 4.4 (d, 1H), 4.7 (d. 2H), 5.1 (m, 1H), 5.3 (t, 1H), 5.8 (d, 1H), 6. 6–6, 7(m, 2H), 6. 9–7. 1 (m, 2H), 7.3–7.7 (m, 8H), 8.7 (t, 1H)

INDUSTRIAL APPLICABILITY

Based on the production method of the present invention, it is possible to produce 6-aminomethyl-6,11-dihydro-5H-dibenz[b,e]azepin employing a simple operation requiring no isolation of the intermediates while avoiding the use of high toxic raw materials and also to markedly decrease its production cost.

What is claimed is:

1. A method for producing 6-aminomethyl-6,11-dihydro-5H-dibenz[b,e]azepin comprising the steps of:
   (i) allowing 2-(11H-dibenz[b,e]azepin-6-ylmethyl)-1H-isoindole-1,3(2H)-dione to react with a metal hydride or a metal hydride complex to form N-[(6,11-dihydro-5H-dibenz[b,e]azepin-6-yl)methyl]-o-hydroxymethylbenzamide; and
   (ii) transforming the formed N-[(6,11-dihydro-5H-dibenz[b,e]azepin-6-yl)methyl]-o-hydroxymethylbenzamide into 6-aminomethyl-6,11-dihydro-5H-dibenz[b,e]azepin.

2. N-[(6,11-dihydro-5H-dibenz[b,e]azepin-6-yl)methyl]-o-hydroxymethylbenzamide.

3. The production method of claim 1, wherein the metal hydride or the metal hydride complex is boron hydride.

4. The production method of claim 1, wherein an alcohol or a water based alcohol is further employed as a solvent in the steps (i) and (ii).

5. The production method of claim 1, in the step (ii), N-[(6,11-dihydro-5H-dibenz[b,e]azepin-6-yl)methyl]-o-hydroxymethylbenzamide is processed with an acid or a base.

* * * * *